United States Patent [19]

Heiliger et al.

[11] Patent Number: 5,453,461
[45] Date of Patent: Sep. 26, 1995

[54] BIOLOGICALLY ACTIVE POLYMERS

[75] Inventors: Ludger Heiliger, Leverkusen; Eberhard Kuckert, both of Leverkusen; Antonious Löbberding; Wolfgang Springer, both of Wuppertal, all of Germany

[73] Assignee: Bayer Aktiengesellschaft, Leverkusen, Germany

[21] Appl. No.: 131,368

[22] Filed: Oct. 4, 1993

[30] Foreign Application Priority Data

Oct. 9, 1992 [DE] Germany .................. 42 34 079.9
Jul. 9, 1993 [DE] Germany .................. 43 22 884.4

[51] Int. Cl.$^6$ .................. C08F 8/00; C08G 83/00; C08G 85/00; C09B 69/10
[52] U.S. Cl. .................. 525/54.1; 525/54.11; 525/326.1; 525/327.4; 525/329.5; 525/329.7; 525/330.3; 525/330.7; 525/333.3; 525/374
[58] Field of Search .................. 525/54.1, 54.11, 525/63, 70, 123, 326.1, 327.4, 329.4, 329.5, 329.7, 330.3, 330.7, 333.3, 374

[56] References Cited

U.S. PATENT DOCUMENTS

| | | | |
|---|---|---|---|
| 4,687,732 | 8/1987 | Ward et al. | 435/6 |
| 4,752,638 | 6/1988 | Nowihski et al. | 525/54.1 |
| 4,829,098 | 5/1989 | Hoffman et al. | 522/5 |
| 5,026,785 | 6/1991 | Mage et al. | 525/329.94 |
| 5,045,480 | 9/1991 | Johnson et al. | 436/532 |
| 5,326,692 | 7/1994 | Brinkley et al. | 435/6 |
| 5,374,516 | 12/1994 | Sutton et al. | 435/5 |

FOREIGN PATENT DOCUMENTS

| | | |
|---|---|---|
| 302715 | 2/1989 | European Pat. Off. . |
| 323692 | 7/1989 | European Pat. Off. . |
| 350233 | 1/1990 | European Pat. Off. . |
| 462644 | 12/1991 | European Pat. Off. . |
| 4034461 | 5/1992 | Germany . |
| WO89/05329 | 6/1989 | WIPO . |

*Primary Examiner*—Nathan M. Nutter
*Attorney, Agent, or Firm*—Connolly & Hutz

[57] ABSTRACT

The present invention relates to novel, biologically active polymers, methods for their preparation and their use for biochemical identification reactions and/or for further reaction with biologically active molecules such as, for example, proteins or nucleic acids.

13 Claims, No Drawings

BIOLOGICALLY ACTIVE POLYMERS

The present invention relates to novel biologically active polymers, processes for their preparation and their use for biochemical identification reactions and/or for further reaction with biologically active molecules such as, for example, proteins or nucleic acids.

In WO 89/053 29 polymer surfaces of manufactured, per se water-insoluble polymers, such as microtitration platelets made from polystyrene or polymethylmethacrylate are modified by means of photochemically active, biotinised compounds in aqueous solution using a polymer-like photoreaction. The photochemical bonding of the photochemically reactive monomeric compound to the polymers takes place in heterogeneous phase with the part of the polymer wetted by the solution, i.e. only at the surfaces of the two phases which are in contact with each other. The high surface tension of water, which is reflected in the poor wettability of the plastic platelets, also provides for extremely poor contact of the two components which are intended to react. This produces a low quantum yield for the photo-bonding reaction and a long irradiation time (1.5 h) is required in order to perform bonding reactions successfully. The solid polymer surface which is randomly functionalised in this way can in principle still only achieve the immobilisation of biomolecules via the per se known biotin—avidin—(or streptavidin-) biotin—biomolecule sequence. Thus it is also necessary initially to subject the biomolecule to be immobilised to a functionalising process using biotin. Therefore, the actual immobilisation of a biotinylated biomolecule is only experimentally possible over an extremely narrow range of concentrations because (strept-)avidin, which is a multi-functional reagent as compared with biotin, may react both as a bridging member in the bonding sequence and also as a masking substance (i.e. cross-linking between the individual polymer molecules of the titration platelets). This means that at low concentrations of the biotin anchor groups, bonding to (biotinylated) biomolecules via (strept-)avidin can only proceed at low yields, while at high concentrations of biotin anchor groups, there is complete cross-linking with the microtitration platelets and thus bonding to (biotinylated) biomolecules can no longer take place.

In comparison, polymers according to the invention can bond to biomolecules such as nucleic acids or proteins in homogeneous phase and thus can be used not only for direct, specific immobilisation, but also in addition to quantify biomolecules via a specific biochemical identification reaction. No cross-linking occurs in the bonding reaction, even at high conversion, due to the specific incorporation of the biologically active section.

Biologically active polymers of the general formula (I) have now been found $$P—(A)_q \quad (I)$$

in which
P represents a polymer component,
A represents a biologically active section and
q is the number 1 or 2.

Suitanble biologically active sections A are for example biotin, digoxigenin, digoxin, digitoxigenin, digitoxin and oligonucleotides made from 1 to 80, preferably 15 to 50, and in particular 20 to 35 nucleotide units. Biotin, digoxigenin and oligonucleotides made from 15 to 50, particularly 20 to 35 nucleotide units are preferred.

The polymer components P may be linear, branched or cross-linked and can be prepared, for example, by radical polymerisation or polycondensation. Polyurethanes and polyureas are also suitable.

Suitable monomer units for the polymer components are, for example, acrylic, methacrylic, vinyl or styryl derivatives or mixtures thereof. These may be, for example, their acid, ester, amide or ketone derivatives.

Suitable monomer units are preferably compounds of the formula (II)

in which
Z represents hydrogen, a $C_1$–$C_{20}$-alkyl, preferably $C_1$–$C_{15}$-alkyl, in particular $C_1$–$C_6$-alkyl, —CO—$OR^2$, —CO—$NR^3R^4$ or —$OOCR^5$ group and
$R^1$, $R^2$, $R^3$, $R^4$ and $R^5$, independently of each other, represent hydrogen or a $C_1$–$C_{20}$-alkyl, preferably $C_1$–$C_{15}$-alkyl, in particular $C_1$–$C_6$-alkyl group.

Other suitable monomer units are preferably styrene, α-methylstyrene or compounds of the formula (III)

in which
$R^6$ represents hydrogen or methyl,
$R^7$ represents $CH_2$ or $SO_2$,
m is zero or 1 and
X represents halogen, $SO_2$—$CH_2$—$CH_2$-halogen, OMe, SO—$CH_3$ or methyl.

Here halogen preferably represents chlorine, bromine or iodine, especially chlorine or bromine, and Me represents an equivalent of a metal, for example sodium, potassium or caesium, or ammonium.

Also suitable are 1- and 2-vinylnaphthalene, 1-vinylcarbazole and compounds which are analogous to those of formula (III) which contain, however, naphthalene or carbazole as the aromatic parent substance, as well as (meth)acrylamides and (meth)acrylates deriving from aromatic amines, phenols, aromatic hydroxycarboxylic, hydroxysulphonic, aminocarboxylic and aminosulphonic acids of the formula (IV)

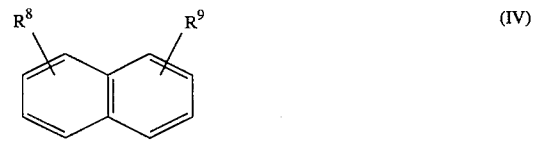

in which
$R^8$ represents hydrogen, $SO_3H$, COOH, $SO_3Me$ or COOMe, wherein Me represents an equivalent of a metal such as for example sodium, potassium or caesium, or ammonium, and $R^9$ represent

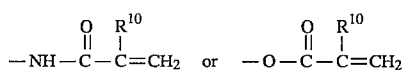

where
$R^{10}$=hydrogen or methyl.

The polycondensates, polyurethanes or polyureas are known, their general methods of preparation being described in Houben-Weyl, Makromolekulare Chemie, part 1, (1987), p. 555–608. In addition a large number of these polymers specified for different applications are described in more detail in part 2, p. 1443–1457 and 1561–1751.

The monomer units mentioned above may be combined with each other in the form or statistical, alternating or branched block, graft or cross-linked polymers. Statistical copolymers and homopolymers are preferred.

Non-cross-linked, non-ionic polymers P have average molecular weights ($\bar{M}w$) between 1 000 and 10 000 000, preferably between 5 000 and 2 000 000. Polycondensation products preferably have average molecular weights between 5 000 and 100 000.

Ionic polymers generally have an intrinsic viscosity of at least 0.1 dl/g, preferably 0.5 to 20, in particular 1–10 dl/g measured in 0.9% strength aqueous NaCl solution at 20° C.

The monomer units may contain reactive or activatable groups which enable covalent bonding to, for example, a chelating agent. These types of groups may be, for example, acid halide, imidester, benztriazolyl, isocyanato, isothiocyanato, oxirane or diimide groups. Monomer units carrying reactive groups which may be mentioned are, for example, (meth)acrylic acid chloride, N-hydroxy-succinimide (meth)acrylate, N-hydroxy-phthalimide (meth)acrylate, N-(meth)acryloyl benztriazole, 3- or 4-isothiocyanatophenyl (meth)acrylate, 2-isocyanatoethyl (meth)acrylate, isocyanatoisopropenylbenzene, isopropenyl-α,α-dimethylbenzyl isocyanate, vinyloxirane or a combination of (meth)acrylic acid and carbodiimides.

As chelating agents within the scope of the invention are to be understood all structures which are capable of reversibly complexing mono-, di- or tri-valent metal ions.

Possible chelating agents are, for example,

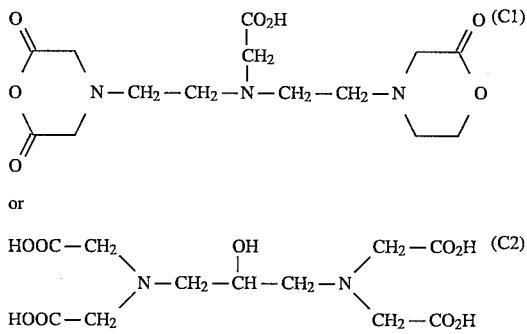

(Sometimes after opening cyclic acid anhydride groups).

The following compounds may be mentioned as monomer units with chelating groups:

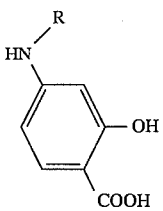

in which

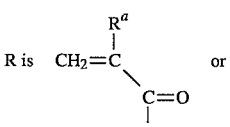

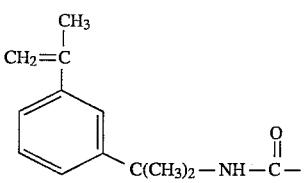

where
$R^a$=H, CH$_3$

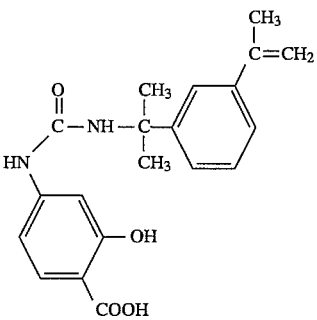

where
R=H, CH$_3$

A large number of suitable chelating agents are described in L. Yuanfang and W. Chuanchu, Pure and Applied Chemistry, Vol. 63 No. 3, 427–463 (1991).

If chelating groups are present in biologically active polymers, the proportion of monomer units with chelating groups is preferably 10–90, particularly 30–80% by weight with respect to 100% by weight of total polymer.

The monomer units in component P may also contain ionic or non-ionic groups which render them water-soluble. The monomers preferably contain ionic groups which render them water-soluble.

Preferred monomer units contain water-solubilising groups in order to impart water solubility to the polymer, which is of advantage for subsequent bonding to biologically active substrates. Carboxylic acid and sulphonic acid groups and their conjugated bases are particularly preferred from among the water-solubilising groups. Particularly preferred are polymer components P which act as chelating agents towards mono-, di- and tri-valent cations such as, for example, lanthanides, particularly europium.

These may be, for example, salts of p-styrylsulphonic acid (Na$^+$, K$^+$, NH$_4$), acrylic acid, methacrylic acid, acrylamide, methacrylamide or derivatives thereof. Suitable derivatives are e.g.: 2-acryloylamino-2-methyl-propanesulphonic acid, dialkylamino-alkyl-(meth)acrylates and dialkylamino-alkyl-(meth)acrylamides such as dimethylaminoethyl methacrylate, dimethylamino-propyl acrylamide and the quaternary compounds deriving from such (meth)acrylates and (meth)acrylamides. Also suitable are, for example: N-vinylpyrrolidone, N-vinylpiperidone, N-vinylcaprolactam, N-vinylformamide, N-vinylacetamide, N-vinyl-N-methylacetamide and N-vinyl-O-methyl-urethane.

The amount of monomer units with water solubilising groups in the whole polymer is preferably 10 to 90% by weight, particularly 20 to 70% by weight, with reference to 100% by weight of total polymer.

Component P may contain, apart form chelating and/or water solubilising groups, dyes, particularly fluorescent dyes. The polymer component preferably contains dyes.

Suitable fluorescent dyes are for example coumarins of the formula (Va)

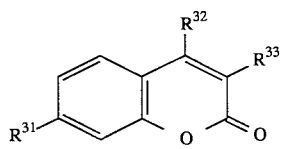

in which
$R^{31}$ represents an O-alkyl, N(alkyl)$_2$, NH-alkyl, NH—SO$_2$-alkyl, O-trimethylsilyl or NH—SO$_2$-aryl group,
$R^{32}$ represents hydrogen, cyano, chloro, hydroxy, an alkyl or aryl group and
$R^{33}$ represents phenyl or a hetero-aryl group.

Here alkyl preferably means $C_1$ to $C_6$ alkyl, aryl preferably means phenyl, alkylene preferably means $C_1$–$C_6$ alkylene and hetero-aryl preferably means (benz)thiazolyl

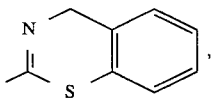

$R^{31}$ may also represent

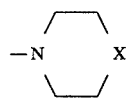

wherein X represents oxygen, a N—$C_1$–$C_4$-alkyl group or (CH$_2$)$_n$, where n may be 0 or 1.

Also suitable are coumarins of the formula (Vb)

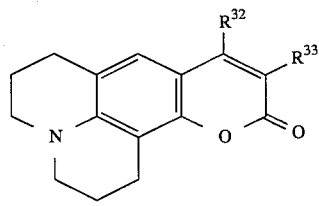

in which $R^{32}$ and $R^{33}$ are as defined above for formula (Va).

The coumarins of formula (Va) and (Vb) preferably contain a functional group on one of the substituents $R^{31}$, $R^{32}$ and $R^{33}$ for bonding the dye to a monomer unit or the polymer obtained therefrom. NH$_2$ or OH groups are particularly suitable for this.

Also suitable are carbostyriles of the formula (Vc)

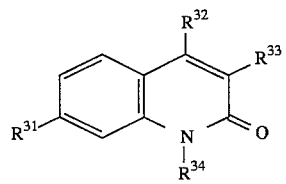

in which
$R^{31}$, $R^{32}$ and $R^{33}$ are defined as above for the coumarins (see formulas (Va) and (Vb)) and
$R^{34}$ represents an alkyl group, preferably $C_1$–$C_6$-alkyl.

Here again one of the substituents preferably contains a functional group for bonding to the monomer unit or the polymer obtained therefrom.

Furthermore, pyrazolines of the formula (Vd) are suitable

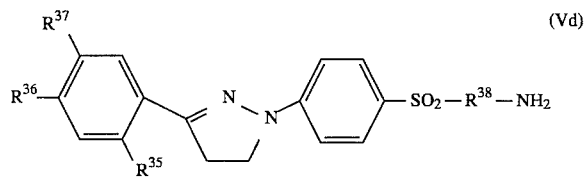

in which
$R^{35}$ represents hydrogen or methyl,
$R^{36}$ and $R^{37}$, independently of each other, represent hydrogen or chlorine and
$R^{38}$ represents an alkylene, alkyl-N-alkylene or alkylene-O-alkylene group,
wherein alkyl and alkylene may represent, for example, a $C_1$ to $C_6$-alkyl or $C_1$ to $C_6$-alkylene group.

Also suitable are naphthalimides of the formula (Ve)

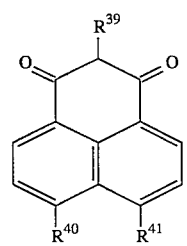

in which
$R^{39}$ represents an alkyl group and
$R^{40}$ and $R^{41}$, independently of each other, represent hydrogen, an O-alkyl or N(alkyl)$_2$ group,
wherein each alkyl preferably represents $C_1$ to $C_6$-alkyl and one of the groups $R^{39}$, $R^{40}$ or $R^{41}$ carries a NH$_2$ group for bonding to a monomer unit or the polymer obtained therefrom.

Also suitable are pyrenes of the formula (Vf)

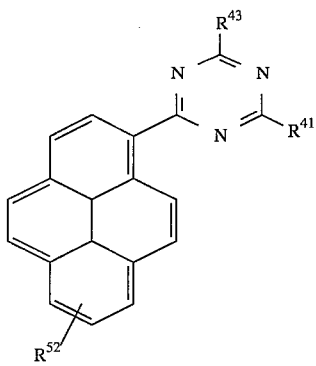

in which
R$^{42}$ represents hydrogen or SO$_3$H and
R$^{43}$ and R$^{44}$, independently of each other, represent an O-alkyl or N(alkyl)$_2$ group,
wherein alkyl preferably represents C$_1$ to C$_6$-alkyl and one of the groups R$^{43}$ or R$^{44}$ carries a NH$_2$ group for bonding to a monomer unit or the polymer obtained therefrom.

Also suitable are fluoresceins of the formula (Vg)

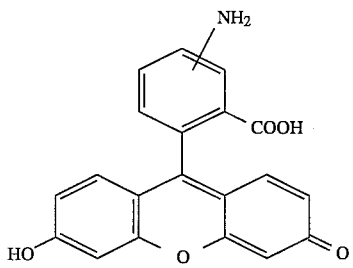

and rhodamines of the formula (Vh)

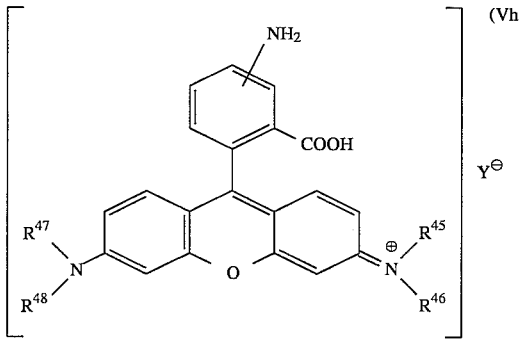

in which
Y$^\ominus$ represents a colourless anion, e.g. Cl$^e$, Br$^e$, I$^e$ HSO$_4^e$,

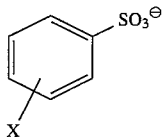

X=Cl, Br, I, CH$_3$ and

R$^{45}$ to R$^{48}$, independently of each other, represent an alkyl group or

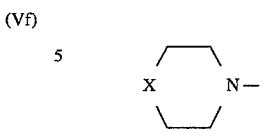

wherein alkyl preferably represents C$_1$ to C$_6$-alkyl and X represents oxygen, a N—C$_1$ to C$_4$-alkyl group or (CH$_2$)$_n$, where n may be zero or 1.

$^\oplus$NR$^{45}$R$^{46}$ and/or NR$^{47}$R$^{48}$, together with the aromatic rings to which they are bonded, may also form a polycyclic system, e.g. of the formula (Vi) or (Vk).

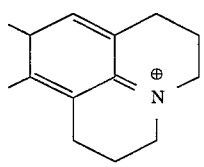

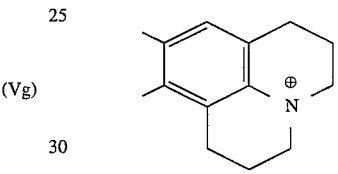

These and other suitable dyes are known (see, e.g. "The Chemistry of Synthetic Dyes", Vol. V, Academic Press (1971) and "Fluorescent Whitening Agents", G. Thieme Verlag Stuttgart (1975)).

Coumarins, fluoresceins and rhodamines are preferred.

Component P preferably contains up to 99% by weight, particularly 5 to 50 and quite particularly preferably 10 to 40% by weight of dye-containing monomer units, with reference to the total polymer. The residual amount of monomer in component P preferably contains water-solubilising groups.

In detail, for example, the following polymers of the formula (I) according to the invention may be mentioned
biotin-polymer 1
biotin-polymer 2
biotin-polymer 3
biotin polymer 4
biotin-polymer 5
oligonucleotide-polymer 5

Monomer unit for polymer 1 with chelating group:

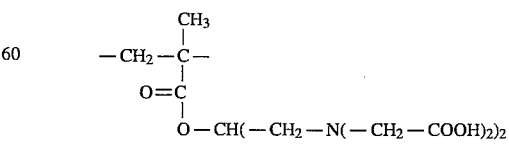

Monomer unit for polymer 2 with chelating group:

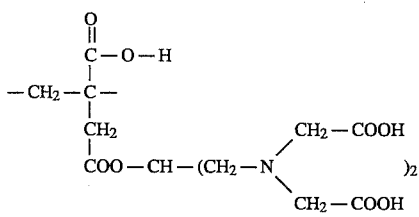

Monomer unit for polymer 3, with chelating group:

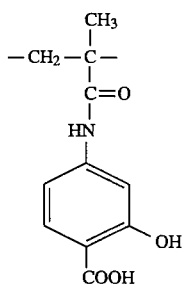

Monomer unit for polymer 4 with chelating group:

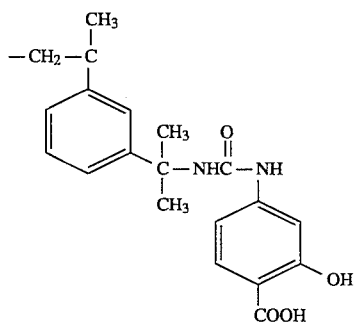

Monomer unit for polymer 5:

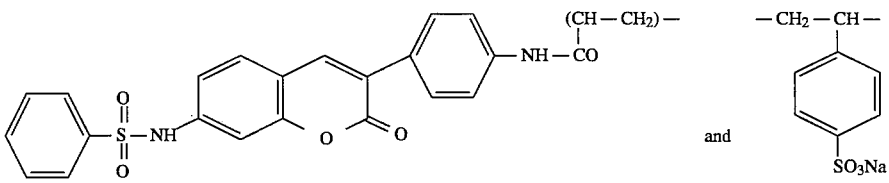

In addition, biologically bondable polymers according to the invention may contain radical chain initiator groups, depending on the type of preparation, which correspond to the groups B–L in formula (VII).

The units A and P in the polymers according to the invention are bonded to each other, for example, via an ester, sulphonic ester, amide, sulphonamide, urethane, thiourethane, urea, thiourea, ether, amine or sulphide group. If increased mobility of the units A and/or P is desired, groups such as, for example, $C_1$–$C_{20}$-alkylene, preferably $C_3$–$C_{15}$-alkylene, in particular $C_5$–$C_{10}$ alkylene, $C_6$–$C_{10}$-arylene-$C_2$–$C_{10}$-alkylene, preferably phenylen- or naphthylen-$C_2$–$C_8$-alkylene, or $(CH_2—CH_2—O)_l$ where $l=1$–20, preferably 3–15, in particular 5–10, may be incorporated between the bonding groups.

Preferably, units A and P are bonded via an amide, urea, ester, ether or urethane group, amide, polyether and urea groups being particularly preferred.

The monomer units are generally known. The polymer component P can be prepared by generally known polymerisation processes.

Thus, for example, vinyl monomers are (co)polymerised under the usual conditions of radical polymerisation with radical chain initiators which contain the biologically active section A, i.e. at temperatures of 30° to 150° C., if desired, or reacted, in the case of solid reactants, in an (inert) solvent such as, for example, dimethylacetamide, dimethylformamide, dimethyl sulphoxide, (chlorinated) aromatic compounds, (chlorinated) aliphatic compounds, ethers, esters, ketones, alcohols, at atmospheric pressure or else, in the case of gaseous monomers, under excess pressure in an autoclave. If it is desired, the usual additives such as ($M_w$ controller such as, for example, dodecanethiol or n-butanethiol, cross-linkers when preparing beads such as, for example, divinylbenzene, etc.) may be added to the reaction solution.

The radical chain initiator (compounds of the formula (VII), see below) containing the biologically active section A may be obtained, for example, by reacting compounds carrying amino or hydroxyl groups which contain the biologically reactive section A with radical initiators which carry (sulphonic) acid chloride or isocyanate groups.

The biologically active section A, which is contained in polymers of the formula (I), is obtained using new biologically active initiators of the general formula (VII)

$$A—L—B—(—L—A)_y \qquad (VII)$$

in which A is the biologically active section defined above,
B represents a radical forming section and
L represents a linker group and
y is the number 0 or 1.
The following groupings are suitable as linker groups L:
—$SO_2$—, —COO—, —$SO_2$NH—, —CO—NH—, —NH—CO—O—, —NH—CS—O—, —NH—CO—NH—, —NH—CS—NH—, —O—, —NH—, —S—.

Preferred linker groupings are —CO—NH—, —NH—CO—NH—, —COO—, —NH—CO—O. The groups —CO—N— and —NH—CO—NH— are particularly preferred.

The linker grouping L covalently bonds together the biologically active section and the radical-forming section B.

If increased mobility of units A and/or B is desired, a spacing function may also be exerted by L, wherein L may then consist of the following sub-units of the formula (VIII):

$$L^1—R—L^1 \quad \text{(VIII)}$$

in which

L¹ is defined as for L above, and

R represents a $C_1$–$C_{10}$-alkylene, preferably $C_3$–$C_{15}$-alkylene, particularly preferably $C_5$–$C_{10}$-alkylene, $C_6$–$C_{10}$-arylene-$C_2$–$C_{10}$-alkylene, preferably phenylen- or naphthylen-$C_2$–$C_8$-alkylene group or $(CH_2—CH_2—O)_n$, where n is 1 to 20, preferably 3 to 15 and particularly preferably 3 to 10.

The following compounds are suitable as the radical-forming section B:

1) azo-structures of the general formula (IX)

$$R^{11}—N=N—R^{12} \quad \text{(IX)}$$

in which $R^{11}$ and $R^{12}$ represent a $C_1$–$C_{20}$-alkyl, $C_3$–$C_{10}$-cycloalkyl, $C_7$–$C_{20}$-aralkyl group or the group

and

Y represents CN, $N_3$ or

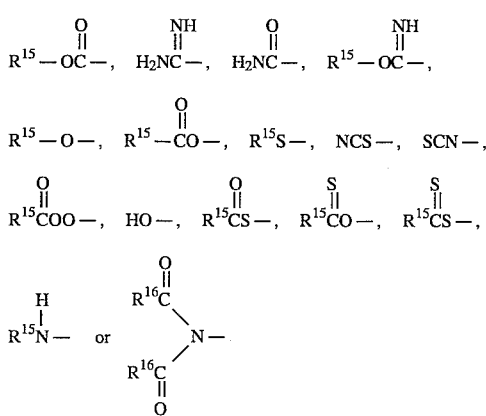

$R^{13}$, $R^{14}$ and $R^{15}$, independently of each other, represent a $C_1$–$C_{20}$-alkyl, $C_3$–$C_6$-cycloalkyl or, if $R^{13}$ and $R^{14}$ are connected, $C_2$–$C_{30}$-alkylene group or in addition one of the groups $R^{13}$ or $R^{14}$, but not both simultaneously, represents phenyl, toluyl, benzyl or phenethyl, $R^{16}$ independently represents a $C_1$–$C_6$-alkyl, $C_3$–$C_6$-cycloalkyl or $C_6$–$C_{12}$-aryl group;

2) tetraaryl/alkylethanes of the general formula (X)

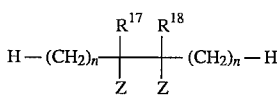

in which

Z represents a hydroxy, $C_1$–$C_6$-alkyl or $C_6$–$C_{20}$ group, particularly hydroxy, methyl, ethyl, n- or iso-propyl, phenyl or naphthyl, $R^{17}$ and $R^{18}$, independently of each other, represent a $C_1$–$C_6$-naphthyl group, in particular methyl, ethyl, n- or isopropyl, phenyl or naphthyl and n represents the numbers 1 to 6, preferably 1, 2, 3, 4 or 5;

3) dinitriles of the formula (XI)

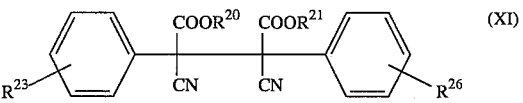

in which $R^{20}$, $R^{21}$ and $R^{23}$, independently of each other, represent $(CH_2)_m$—H, in which m represents the numbers 1 to 6, preferably 1, 2, 3, 4 or 5;

4) peroxides of the general formula (XII)

in which l represents the numbers 0 to 6, preferably 0, 1, 2, 3 or 4, in particular 0, 1 or 2 and $R^{24}$ represents a phenylene, naphthylene, $C_3$–$C_6$-alkylene or $C_3$–$C_6$-cycloalkylene group.

The structures mentioned under 1) and 4) are preferred for unit B.

The compounds of the formulas (IX) to (XII) are generally known (see, for example, U.S. Pat. No. 3,956,269, Houben-Weyl, Makromolekulare Stoffe, part 1, p. 16–19).

Preferred azo structures of the formula (IX) are compounds of the formula (IXa)

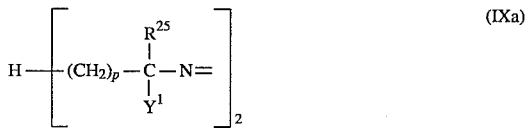

in which p represents the numbers 1 to 20, preferably 1 to 15, in particular 2 to 10, $Y^1$ represents CN, $N_3$, $COOR^{26}$ and $R^{25}$ and $R^{26}$, independently of each other, represent a $C_1$–$C_6$-alkyl group, particularly methyl, ethyl, n- or iso-propyl, or a $C_3$–$C_6$-cycloalkyl group, particularly cyclopropyl, cyclopentyl or cyclohexyl.

A particularly preferred structure for the unit B mentioned under 1) has the formula (IXb)

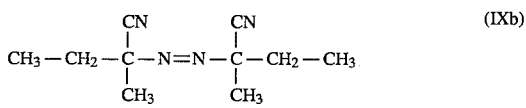

i.e. p is 2, $R^{25}$ is $CH_3$ and $Y^1$ is CN.

A particularly preferred structure for the unit B mentioned under 4) corresponds to the formula (XII) with l=0 and $R^{24}$=phenylene.

The structures of the formulas (IX) to (XII), which make up the radical-forming section, carry 1 (y in formula VII=0) or 2 (y in formula (VII)=2) reactive groups $X^1$ (see description of formula (XIII)).

In the azo structures of the formula (IX), the $R^{11}$ and $R^{12}$ groups carry this/these group(s). In the structures of the formulas (IXa), (IXb), (X) and (XII), the terminal hydrogen atoms are replaced by this/these group(s). The dinitriles of the formula (XI) carry this/these group(s) symmetrically about the central bond on $R^{20}$, $R^{21}$ and/or $R^{23}$.

In detail, for example, the following biologically active initiators of the formula VII are pointed out.

Initiator 1:

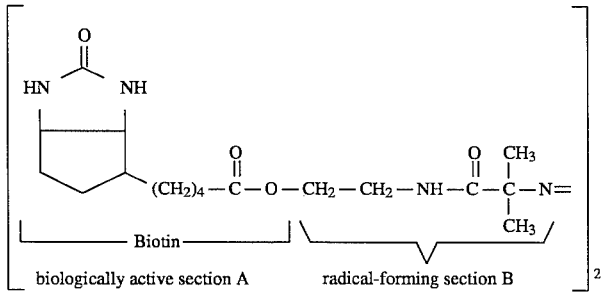

Initiator 2:

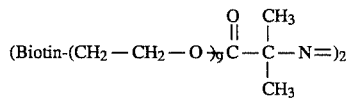

Initiator 3:

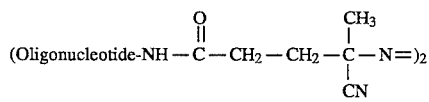

Initiator 4:

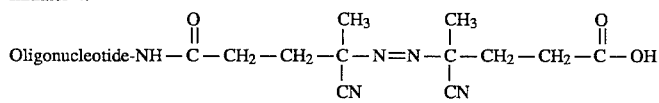

Initiator 5:

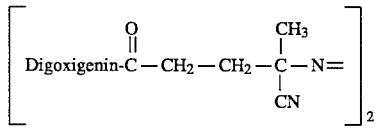

Initiator 6:

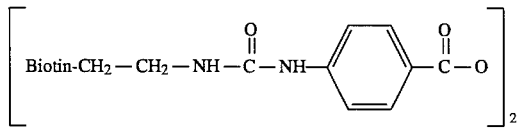

Initiator 7:

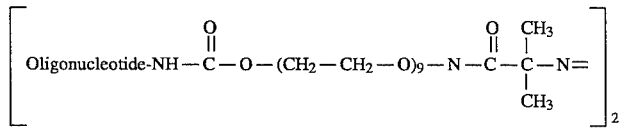

The biologically active radical chain initiators of the general formula (VII)

$$A\text{—}L\text{—}B\text{—}(\text{—}L\text{—}A)_y \qquad (VII)$$

are prepared by reacting radical-forming compounds of the general formula (IX)

$$X^1\text{—}B\text{—}(X^1)_y \qquad (XIII)$$

wherein
B is defined as above and
$X^1$ may be NCO, NCS, COCl, COOH, CO—O—NH-hydroxysuccinimide, OH, $NH_2$, SH, Cl, Br or I and
y is 0 or 1, preferably 1,
with 1 or 2 equivalents of biologically active substance A in solvents which are chemically inert to the groupings mentioned under $X^1$ such as, for example, chlorinated aliphatic compounds, ketones, nitriles, sulphoxides, sulphones etc., at temperatures between 0° and 40° C.

In the case of compounds of the general formula (XIII)

$$X^1\text{—}B\text{—}(X^1)_y \qquad (XIII)$$

in which $X^1$ represents COCl or $CONHSO_2Cl$,
a proton acceptor such as, for example, pyridine or triethylamine is expediently added to the reaction mixture, whereas if X=COOH the reaction is performed in the presence of carbodiimides, for example dicyclohexyl-carbodiimide.

Compounds in which $X^1$ represents NCO and CO—O—N-hydroxysuccinimide are preferred for use as the compound of the formula $X^1$—B—$(X^1)_y$ in the process according to the invention.

Reaction takes place preferably between 0° and 30° C., particularly preferably between 15° and 25° C. and in particular at ca. 20° C. Methylene chloride, acetone or acetonitrile are preferably used as solvent.

Compounds of the formula (XIII) are generally known or can be prepared by a generally known process (see, e.g., U.S. Pat. No. 4,155,937).

The linker group L is formed by reacting $X^1$ from the formula $X^1$—B—$(X^1)_y$ with the reactive group in the biologically active unit A, for example the carboxyl group in biotin or the amino group in an oligonucleotide.

Isolation of the biologically active radical chain initiator takes place using known methods, e.g. by evaporating off the solvent under high vacuum after filtering off optionally formed (ionic) side products, if low-boiling solvents are used, or by precipitating by the addition of a suitable precipitating agent, wherein the product according to the invention generally precipitates in the pure form. In cases where the side products are not volatile or cannot be separated from the compounds according to the invention by dissolution or filtration, isolation of the compounds according to the invention takes place by per se known methods of liquid chromatography, for example column chromatography or preparative HPLC (high pressure liquid chromatography).

Preparation of biologically active polymers of the formula (I):

Free radicals which contain the biologically reactive section A are formed by the (thermally) initiated decomposition of the radical chain initiator and these react with the ethylenically unsaturated compounds to give new free radicals which add further ethylenically unsaturated monomers, wherein termination of the propagation reaction takes place by the combination of two propagating radicals, by their disproportionation, the abstraction of hydrogen or by chain transfer (e.g. by using chain transfer agents). On termination by the first reaction, polymers of the formula A—P—A according to the invention are produced, whereas with the latter reactions polymers of the formula A—P according to the invention are produced. In the event of several termination reactions occurring simultaneously, mixtures of polymers with both formulas according to the invention are formed. The molar masses of the polymers according to the invention are adjustable using per se known variations in the experimental details, such as concentration of initiator, monomer or optional chain transfer agent, temperature and solvent.

Radical chain polymerisation may also be initiated using non-functional, conventional radical chain initiators, such as, for example, azoisobutyronitrile or dibenzoyl peroxide, by using a mercapto-containing biologically active section A—SH, wherein the mercapto-containing section A then acts both as chain-transfer agent and as molecular weight controller.

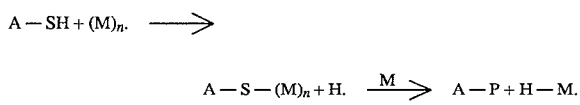

Alternatively, other per se known mono- and bifunctional initiators (AnI) may also be used for anionic polymerisation, in which termination of the propagation reaction may take place after achieving the desired molar mass using functionalisable reagents such as, for example, $I_2$ or Br—CN, whereby the bonding to compounds with hydroxy or amino groups, which contain the biologically active section A, takes place in a polymer-analogous manner:

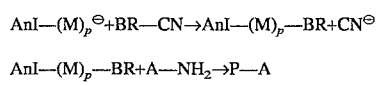

Suitable as a further process for the preparation of dyes according to the invention is the (living) cationic polymerisation of monomers capable of this under per se known conditions, i.e. in the presence of cationic initiators (CatI), wherein the propagation reaction is terminated after achieving the desired molar mass by compounds which contain amino, thio or hydroxy groups and which contain the biologically active section.

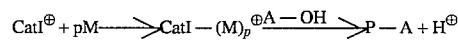

As a modification to living cationic polymerisation, the Inifer method is suitable for preparing polymers according to the invention (see Kennedy, J. P.: Polymer J. 12, 609, (1980)), where the function of initiator and chain transfer agent is performed by one and the same compound.

The functional terminal groups may then be reacted in a polymer-analogous manner with a compound which contains amino or thio groups and the biologically active section A.

A further process which is suitable for preparing polymers A—P—A according to the invention is a polycondensation reaction in which monomers capable of this, such as, for example, diols or diamines and bis-isocyanates or bis-acid chlorides, are subjected to a condensation reaction by per se known methods of polycondensation, termination taking place with compounds which contain the biologically reactive section A after reaching the desired molar mass.

The polymers according to the invention obtained by these processes, if they possess functional groups, are reacted further in per se known polymer-analogous reactions in order to achieve the desired properties, e.g. water solubility.

It is more expedient and simpler to adjust the properties by the polymerisation of appropriate monomers. Here, radically polymerisable monomers, with respect to the versatility of their chemical properties, are superior to other monomers. Therefore, the process of free radical chain polymerisation using radical chain initiators or chain transfer agents which contain the biologically active section A is preferred.

The biologically bondable polymers of the formula (I) according to the invention can be used for immunological purposes such as, for example, gene-probe tests or for immobilising and marking biological substances, such as, for example, DNA.

The following examples are for explanatory purposes only and are not to be interpreted as restricting the type or scope of the present application in any way.

EXAMPLES

A) Preparation of biologically active initiators

Example 1 (Corresponding to Initiator 1)

3 mmol of biotin is stirred for 18 h under pure nitrogen with 1 mmol of 2,2'-azobis[2-methyl-N-(2-hydroxyethyl)-propionamide] and 3 mmol of dicyclohexylcarbodiimide in 20 ml of dry dimethylformamide at room temperature. The precipitate which is produced is filtered off. 1 ml of concentrated aqueous ammonia solution is added to the filtrate. Stirring is continued for one hour at room temperature and filtering is then repeated. The filtrate is poured onto crushed ice, wherein the product according to the invention (initiator 2) is precipitated. The dried and washed precipitate is pure product according to the invention, according to analysis using thin layer chromatography in methanol/chloroform (2:1, $I_2$ detection) and $^1H$ NMR.

Example 2

Preparation of Oligonucleotide Initiators

A solution of 6 mg (12.6 μmol) of 4,4'-azobis(N-hydroxysuccinimidyl 4-cyanopentanoate) in dimethylformamide is added to 1.5 mg (0.26 μmol) of 5'-aminolink oligonucleotide with the sequence ATCCAGTTGTGTCTTCAAC in sodium phosphate buffer (pH=7.5). The reaction mixture was stirred for 72 h at room temperature. The reaction product is isolated by preparative HPLC (high pressure liquid chromatography) on a RP 18 column with an acetonitrile gradient increasing over 30 min in 0.1M triethylammonium acetate. Yield 35% of theory.

B) Biologically active polymers

Example 3

10 g of azobisisobutyronitrile (AIBN) as well as 100 g of polyethylene oxide (molecular weight 400) and polyol E 400 are added to 200 ml of methylene chloride. The solution is cooled to 0° C. and HCl gas is introduced (about 46 g of HCl in 3 hours) until saturation is reached. The resulting clear solution is stirred overnight at 0° C. and then poured slowly with stirring onto 200 g ice/100 g water. After stirring for 2 hours the two phases are separated in a separating funnel, the aqueous phase is subsequently extracted 3 times with methylene chloride and the combined phases are extracted by shaking with an aqueous $NaHCO_3$ solution and water. The organic phase is dried over $Na_2SO_4$ and evaporated in a rotary evaporator at room temperature under a high vacuum. The yield is 41.6 g, corresponding to 70.7% of theory. The $^{14}N$ elementary analysis reveals a content of 3.4% nitrogen (theoretical: 3.1%).

Example 4

$COCl_2$ was introduced into a solution consisting of 5 g of the product from Example 1 in 50 ml of tetrahydrofuran. 5.5 g of a viscous oil remain after evaporating the solution to dryness.

Example 5: Biotinylated Starter=Initiator 2

1 g of $Na_2CO_3$ and 1 g of biotin hydrazide are heated in 15 ml of dimethyl sulphoxide (DMSO) to 75° C. to form a solution. After cooling the solution to 0° C., 2.02 g of the substance from Example 2 are added and the mixture is stirred overnight at room temperature. The precipitate is filtered off and the filtrate is evaporated in a rotary evaporator; the residue is taken up in chloroform, extracted by shaking with a $NaHCO_3$ solution and water and the organic phase is dried over $Na_2SO_4$. After evaporating off the solvent, 1.26 g of a viscous oil remains.

Example 6

Preparation of a biologically active polymer (marking polymer) from an initiator with biotin as the biologically active terminal group.

The following are dissolved in 10 ml of dry dimethyl sulphoxide:

a) 1.5 g of sodium p-styryl sulphonate
b) 0.5 g of coumarin dye 1 and
c) 100 mg of the initiator from example 5

Formula of the coumarin dye:

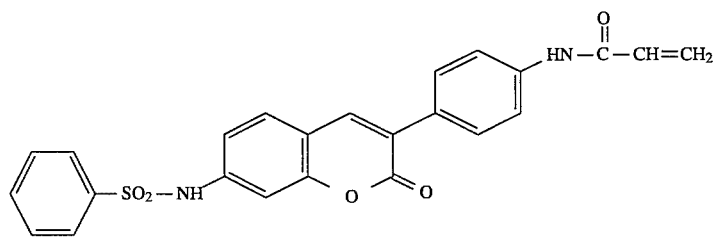

The solution is thoroughly flushed through with pure nitrogen, heated to 70° C. and kept at this temperature for 16 h. The crude mix is precipitated in 200 ml of methanol, filtered under suction, dried and subjected to ultra-filtration (exclusion limit 10 000 Dalton). The water-soluble, fluorescing polymer has an average molar mass of 110 000 Dalton ($M_n$) and may be used directly for reactions with avidin or strepatavidin.

Reaction of biotinylated polymer with streptavidin:

6 μl of streptavidin (conc: 1 mg/ml) are added to a solution of the polymer from example 6 (conc: 6 mg/ml) and shaken for 8 hours at room temperature.

The reaction product is subjected to a SDS gel electrophoresis (in acrylamide). Pure streptavidin and pure polymeric dye are applied for comparison.

After staining with coumassie blue (a dye which reacts with proteins), the result of electrophoresis showed that the streptavidin was fully bonded by the polymer dye. The broad band of reaction mixture was a green colour, while no bands were visible in the streptavidin region. The pure dye was not stained at all by coumassie blue. Despite ultra-filtration, the pure dye had a molecular weight distribution, due to its synthetic type of preparation, which was also transferred to the reaction product, i.e. the streptavidin/polymer coupling product. This coupling product could act as a marker for biotinylated biomolecules, for example anti-bodies, nucleic acids, proteins.

Example 7

Preparation of a marking polymer from an initiator with an oligonucleotide as the biologically active terminal group.

Exactly the same procedure is followed as in example 6, but the initiator from example 2 is used instead of the initiator from example 5 and 1.2 ml of dimethyl sulphoxide are used instead of 10 ml:

a) 0.3 g of sodium p-styryl sulphonate
b) 0.1 g of coumarin dye 1 and
c) 0.5 mg of initiator from example 2.

The polymer has an average molar mass of 500 000 ($M_n$) and may be used directly in gene probe tests to detect DNA or RNA with the complementary sequence to that in the oligonucleotide.

Example 8

Synthesis of monomer 1 for polymer 1:

2 g of 1,3-diamino-2-propanol-N,N,N',N'-tetraacetic acid are dissolved in 30 ml of water and neutralised with 2.5 g of triethylamine, the water evaporated off and the residue taken up in 50 ml of acetonitrile. 0.96 g of methacrylic anhydride and 0.62 g of triethylamine were added to this and heated for 6 h at 50° C. The crude solution is filtered, concentrated by evaporation and adjusted to pH 3 with 1N hydrochloric acid. Then the mixture is concentrated by evaporation and precipitated from acetone.

The product is identified by $^1$H NMR from the characteristic resonance of the methacryl protons at 5.55 and 6.15 ppm. Yield: 56% of theory.

Example 9

Synthesis of monomer 2 for polymer 2:

The same procedure was used as in example 8, but itaconic anhydride was used instead of methacrylic anhydride.

Example 10

Synthesis of monomer 3 for polymer 3:

5 g of p-aminosalicylic acid are dissolved in dimethylacetamide, 3 g of methacrylic anhydride are added and the mixture is heated at 90° C. The crude solution is concentrated by evaporation and poured into water. The precipitate is filtered, rewashed with water and dried.

The product is identified by $^1$H NMR from the characteristic methacryl protons at 5.55 and 6.15 ppm.

Yield: 65% of theory.

Example 11

Synthesis of monomer 4 for polymer 4:

The same procedure was used as in example 10, but α,α-dimethyl-isopropenylbenzyl isocyanate was used instead of methacrylic anhydride.

Examples 12 to 15

Preparation of polymers 1–4:

For polymers 1 and 3 the polymerisation conditions in example 6 were applied using the initiator from example 1 and for polymers 2 and 4 the conditions described in example 7 were applied using the initiator from example 2, with the following monomers:

|           | Monomer 1 | Monomer 2 | Monomer 3 | Monomer 4 | Potassium sulphopropylmethacrylate | Molar mass (—Mn) |
|-----------|-----------|-----------|-----------|-----------|-----------------------------------|------------------|
| Polymer 1 | 2 g       | —         | —         | —         | 2 g                               | 130,000          |
| Polymer 2 | —         | 0.2 g     | —         | —         | 0.2 g                             | 420,000          |
| Polymer 3 | —         | 2 g       | 2 g       | —         | 1 g                               | 115,000          |
| Polymer 4 | 0.1 g     | —         | —         | 0.2 g     | 0.1 g                             | 380,000          |

The polymers are subjected to ultrafiltration with an exclusion limit of 10,000 Dalton and the molar mass tested using aqueous GPC (gel permeation chromatography). The polymers could now be supplied with metal ions and then used to react with (strept)avidin (polymers 1 and 3) or to detect the TA promoter region of the HIV gene (polymers 2 and 4).

Biologically Active Substances Which Are Marked With Marking Polymers

Example 16

Double Marking the Polymer/Oligonucleotide Probe

To detect coupling of the oligonucleotide probe to the polymer and to compare the sensitivity of detection of the coumarin fluorescent dye bonded to the polymer, the polymer/oligonucleotide probes were double marked with conventional phosphorus[32] ($P^{32}$) or digoxigenin markers.

The reactive 5'-amino-oligonucleotide probe with the 19-fold nucleotide sequence 5'd ATCCAGTTGTGTCT-TCAAC from example 2 was marked at the 3'end with alpha $P^{32}$-dCTP using an end-marking kit from the Boehringer Mannheim company. Alternatively, the end group was marked in a non-radioactive manner using digoxigenin-dUTP. Ca. 50% end marking was achieved after 60 minutes at 37° C. in a 50 µl batch using 10 µl of reaction buffer (potassium cacodylate 1 mol/l; tris/HCl 125 mmol/l; beef serum albumin 1.25 mg/ml; pH 6.6; 25° C.) 1–2 µg of oligonucleotide, 5 units of terminal transferase cobalt chloride (CoCl$_2$); 2.5 mmol/l and 25 µCi of alpha P$^{32}$dCTP.

Coupling to the polymer was performed as described in example 7.

The polymer was precipitated in ethanol and then dissolved in 1 ml of doubly distilled water. Gel electrophoresis in 17% strength polyacrylamide gel proved that the oligonucleotide had bonded to the polymer.

Using the double marked polymer/oligonucleotide probe, which enabled detection via the fluorescence of the coumarin fluorescent dye bonded to the polymer or detection via the P$^{32}$ or digoxigenin bonded to the oligonucleotide, slot hybridisation was performed as described in example 17 below and liquid hybridisation was performed as described in example 18.

Example 17

Slot Blot Hybridisation Using the Polymer/Oligonucleotide Probe

Hybridisation was performed by the usual method at an incubation temperature of 40° to 68° C. Depending on the temperature of hybridisation, different substances were added. Dextrane sulphate or other polymers were used to increase the rate and extent of hybridisation. Detergents and masking reagents such as dry milk, Denhardt's solution, heparin or sodium dodecyl sulphate (called SDS in the following) were added to suppress non-specific bonding of DNA to the membrane. Denaturing agents such as urea or formamide could be used to lower the melting point of the hybrids so that lower temperatures of hybridisation could be used. In addition, non-specific bonding of gene probes to non homologous DNA on the blot could be reduced by the addition of heterologous DNA.

To prepare for hybridisation, 50–500 ng of unmarked genomic DNA from Nitrosomonas europae were initially denatured for 5 minutes at 100° C., cooled to 0° C. and then applied to pre-treated nitrocellulose or nylon membranes using a Minifold II filtration apparatus from Schleicher and Schüll and fixed at 80° C. for 2 hours. The filters were hybridised at 68° C. for at least 1 hour in a sealed plastic foil sachet or plastic box with at least 20 ml of hybridising solution per 100 cm$^2$ of filter.

The solution was replaced by 2.5 ml per 100 cm$^2$ of filter of hybridising solution to which were added 100 ng of the polymer/oligonucleotide probe from example 13. The filters were incubated for at least 6 hours at 68° C. with slight shaking.

The filters were than washed for 2×5 minutes at room temperature with at least 50 ml 2×SSC, 0.1% SDS per 100 cm$^2$ of filter and 2×15 minutes at 68° C. with 0.1×SSC, 0.1% SDS.

The filters were then used directly to detect hybridised DNA.

| Solutions: | |
|---|---|
| 20 × SSC: | 3M NaCl, 0.3 M Na citrate pH 7.0 |

| Solutions: | |
|---|---|
| Hybridisation solution 1: | 5 × SSC; 0.1% N-lauroyl sarcosine, Na salt; 0.02% SDS; 0.5% masking reagent (Boehringer Mannheim) solution to dissolve at 50–70° C. |

Other hybridisation solutions, which could also be used for slot blot hybridisation are e.g.:

| Hybridisation mix 2: | 50% formamide 7 × SSC; 2 × Denhardt's solution (100 × Denhardt's: 2% ficoll, 2% polyvinylpyrrolidone, 2% beef serum albumin) 300 µg/ml of calf thymus DNA |
|---|---|
| Hybridisation mix 3: | 6 × SSC; Denhardt's solution; 50 µg herring sperm DNA, beef serum albumin 0.1% |
| Hybridisation mix 4: | 5 × SSC; PEG; 5% dried milk powder 0.01 M sodium pyrophosphate; |

Detection was effected via the coumarin fluorescent dye bonded to the polymer in the oligonucleotide probe. The fluorescing slot blots on the filter were evaluated quantitatively in a Shimadzu CS 930 scanner.

Evaluation of the hybridisation test was also possible using autoradiography due to double marking of the oligonucleotide with P$^{32}$ by 3'end marking using terminal transferase. In this case, the filter was fixed to a glass plate and then laid on an X-ray film and exposed for 2–5 hours. After developing the film, blackening of the slot blots was evaluated quantitatively with a Shimadzu scanner.

Alternatively, another method of detection was also used. Using polymer/oligonucleotide probes marked with digoxigenin, a dye detection was performed using alkaline phosphatase conjugated anti-bodies and bromo-chloro-indolyl phosphate and nitroblue tetrazolium or a chemiluminescent Read Out with alkaline phosphatase and AMPPD (3(2'-spiroadamantan)-4-methoxy-4-(3"-phosphoryloxy)-phenyl-1.L-dioxetan) as substrate.

Direct comparison of the sensitivity of different detection systems was possible by means of double marking.
Results:

By signal amplification of the coumarin dye molecules in the polymer (ca. 200 dye molecules/polymer) in the oligonucleotide probe, approximately the same sensitivity could be achieved for the detection of 1–0.1 pg of DNA as when using enzymatic methods of detection. The use of a polymer carrier for the coumarin dye molecule produces a 100–1000 times higher sensitivity than conventional marking with fluorescent dyes via fluorescent nucleotide units.

Example 18

Liquid Hybridisation Using Polymer/Oligonucleotide Probes

Liquid hybridisations were performed as sandwich hybridisations with streptavidin coated magnetic particles from the Dynal (Hamburg) company to separate the hybridisation complex.

Liquid hybridisation tests were performed as sandwich tests with 100 ng of 5'-biotinised capture oligonucleotide probes with the nucleotide sequence 5'd CTGCTCGTAGA-CAATGCGT, 100 ng of polymer/oligonucleotide probe as in example 16 (detector gene probe) and Nitrosomonas Target DNA at different concentrations (50 ng–1 000 ng) in a volume of 50 μm.

After heating for 10 minutes at 100° C. and then cooling to 0° C., 50 μl of 2×hybridisation mix 1 (Boehringer Mannheim) were added and hybridised for 1 hour at 68° C. The magnetic beads were pre-treated with 1×hybridisation mix 1 and the liquid was pipetted off after separating over a magnet and the hybridisation batch was added and incubated for ½ hour at room temperature with slight agitation. The coupled hybridisation complex was separated with the beads, the residual liquid was pipetted off and the beads were washed once with buffer A (2×SSC; 0.1% SDS), then twice with buffer B (0.1% SSC; 0.1% SDS).

Finally 500 μl of double distilled $H_2O$ were added and the fluorescence of the polymer/oligonucleotide in the hybridisation complex was measured in a fluorescence photometer with 375 nm excitation and 495 nm emission.

In parallel with this, the masking reaction and antibody reaction to detect hybridisation via chemiluminescence was performed. The beads loaded with DNA were treated once with 150 μl of wash-buffer (0.1M maleic acid, 0.1M NaCl, pH 7.5, 0.3% tween 20) and after separating and pipetting off the wash-buffer, 400 μl of buffer 2 (0.1M maleic acid; 0.15M NaCl; pH 7.5; 1% masking reagent (Boehringer, Mannheim) were added. After ½ hour of incubation at room temperature, this was separated, pipetted off and 100 μl of anti-body conjugate solution (AB 1:10 000 in buffer 2) were added and incubated for ½ hour at room temperature, then separated, pipetted off and treated with 400 μl of wash buffer, 2×15 minutes with slight agitation. Finally the mix was separated and treated with 150 μl of buffer 3 (0.1 M tris/HCl buffer with 0.1M NaCl and 50 mM $MgCl_2$ pH 9.5). It was then separated again and incubated with detection solution using AMPPD 1:100 in buffer 3 for 15 minutes at 37° C. on a water bath, then the chemiluminescence was measured in a luminescence photometer at 477 nm (Luma-counter from Lumac).

Results

By signal amplification of the coumarin dye in the polymer, a much higher sensitivity was achieved than with direct fluorescence marking of DNA. The sensitivity was 100–1000 times higher. The detection limit achieved with 1–0.1 pg of DNA was approximately that of chemiluminescence sensitivity.

Example 19

Hybridisation of the Polymer/Oligonucleotide Probe with Amplified DNA

Due to this increase in sensitivity, direct and thus particularly simple detection via fluorescence of the polymer/oligonucleotide becomes a very good alternative as compared with the known techniques of detection such as chemiluminescence, bromochloroindolyl phosphate/nitroblue-tetrazolium dye reaction and radioactive methods.

Amplification of the target DNA was performed by the polymerase chain reaction (EP-A 200 362; 201 184) and alternatively by the hairpin amplification method (EP-A 427 074). 2 μg of genomic DNA from Nitrosomonas europae, 2 μmol of primer 1 (5'dATCCAGTTGCTTCAAC) and primer 2 (5'ACTGGCAGGCAGCAG), 2.5 units of Taq polymerase from Cetus/Perkin-Elmer and 200 μmol of dNTPS each time in a total of 100 μl of PCR buffer (50 mM KCl, 10 mM tris/HCl pH 8.3, 1.5 mM $MgCl_2$, and 0.01% of gelatine). Amplification was performed in a PCR processor from Cetus/Perkin-Elmer.

Using the batches, first of all an initial melting of DNA was performed for 2 min 30 sec. at 94° C., then the DNA was denatured for 1 min at 94° C., primer-annealing was performed for 2 minutes at 40°–45° C. and primer extension for 3 minutes at 72° C., per cycle. After 35 cycles there was a final 20 minute extension at 72° C. and then the batches were cooled to 4° C.

The amplified DNA was denatured for 5 minutes at 100° C. and then the batches were immediately cooled to 0° C., 200 μl of ice-cold 20×SSC were added and it was immediately applied to nitrocellulose or nylon membranes using a Minifold II filtration apparatus from Schleicher and Schü ll. The DNA on the filters was fixed for 2 hours at 80° C.

Slot blot hybridisation with the polymer/oligonucleotide probe and detection took place in the same way as described in example 18.

Results

The combination of target nucleic acid amplification and signal amplification of the coumarin dye in the polymer achieved a sensitivity which enabled detection of individual DNA molecules. Evaluation using polymer fluorescence is thus a genuine alternative to sensitive chemiluminescence methods. In contrast with enzymatic formation of chemiluminescence, fluorescence in a polymer may be measured directly.

We claim:

1. A biologically active water-soluble polymer of the general formula (I)

$$P-(A)_q$$

wherein

P represents a polymer component having an average molecular weight of 1,000 to 1,000,000 which is linear, branched or cross-linked, the monomer units for the polymer component being selected from the group consisting of acrylic, methacrylic, vinyl or styryl units or mixtures thereof, and wherein the monomer units optionally contain chelating agents or ionic or non-ionic water-solubilizing groups, and A is a biologically active moiety selected from the group consisting of biotin, digoxigenin, digoxin, digitoxigenin, digitoxin and oligonucleotides having 1 to 80 nucleotide units, and q is the number 1 or 2 and wherein A and P are bonded by an amide, urea, ester, ether, or urethane group.

2. A biologically active polymer according to claim 1, wherein the monomer units are obtained from:

i) compounds corresponding to formula (II)

in which

Z represents hydrogen, a $C_1$–$C_{20}$-alkyl, —CO—$OR^2$, —CO—$NR^3R^4$ or —$OOCR^5$ group and $R^1$, $R^2$, $R^3$, $R^4$ and $R^5$ independently of each other, represent hydrogen or a $C_1$–$C_{20}$-alkyl, and ii) styrene, α-methyl styrene or compounds corresponding to formula (III)

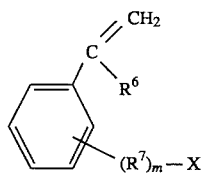 (III)

in which

R⁶ represents hydrogen or methyl,

R⁷ represents $CH_2$ or $SO_2$, m is zero or 1 and

X represents halogen, $SO_2$—$CH_2$—$CH_2$-halogen, OMe, SO—$CH_3$ or methyl, where Me represents an equivalent of a metal, and wherein at least one of the monomers contains an attached dye.

3. A biologically active polymer according to claim 2, comprising the following units as the monomer units:

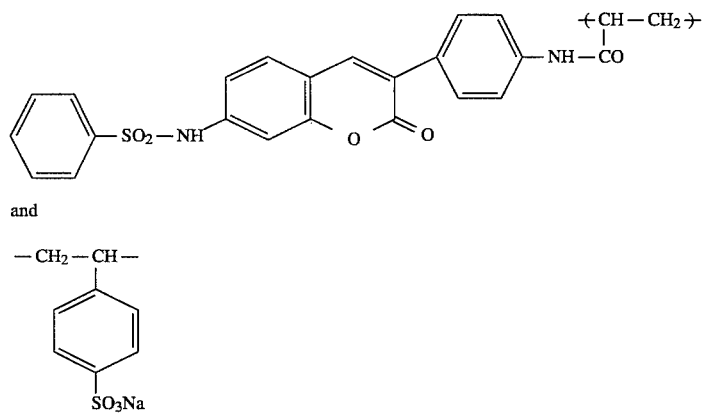

and

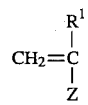

and wherein A is biotin.

4. A biologically active polymer as claimed in claim 2, wherein the dye comprises a coumarin or fluorescein dye.

5. A biologically active water-soluble polymer of the general formula (I)

P—(A)$_q$ wherein

P represents a polymer component having an average molecular weight of 1,000 to 1,000,000 which is linear, branched or cross-linked, the polymer comprising monomer units obtained from i) compounds corresponding to formula (II)

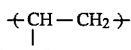 (II)

in which

Z represents hydrogen, a $C_1$–$C_{20}$-alkyl, —CO—OR², —CO—NR³R⁴ or —OOCR⁵ group and R¹, R², R³, R⁴ and R⁵, independently of each other, represent hydrogen or a $C_1$–$C_{20}$-alkyl, and ii) styrene, α-methyl styrene or compounds corresponding to formula (III)

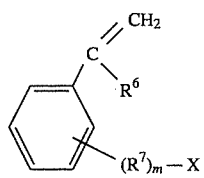 (III)

in which

R⁶ represents hydrogen or methyl,

R⁷ represents $CH_2$ or $SO_2$, m is zero or 1 and

X represents halogen, $SO_2$—$CH_2$—$CH_2$-halogen, OMe, SO-$CH_3$ or methyl, where Me represents an equivalent of a metal, A is a biologically active moiety selected from the group consisting of biotin, digoxigenin, digoxin, digitoxigenin, digitoxin and oligonucleotides having 1 to 80 nucleotide units, and q is the number 1 or 2, and wherein A and P are bonded by an amide, urea, ester, ether or urethane group.

6. A biologically active polymer as claimed in claim 5, wherein the polymer further comprises an additional monomer selected from the group consisting of (meth)acrylic acid chloride, N-hydroxy-succinimide (meth)acrylate, N-hydroxy-phthalimide (meth)acrylate, N-(meth)acryloyl benztriazole, 3- or 4- isothiocyanatophenyl (meth) acrylate, 2-isocyanatoethyl (meth)acrylate, isocyanato-isopropylbenzene, isopropenyl-α,α-dimethyl-benzyl isocyanate, vinyloxirane, and combined (meth)acrylic acid and carbodiimides, to which additional monomer a chelating agent is covalently attached.

7. A biologically active polymer as claimed in claim 5, wherein the chelating agent has the formula C1) or (C2):

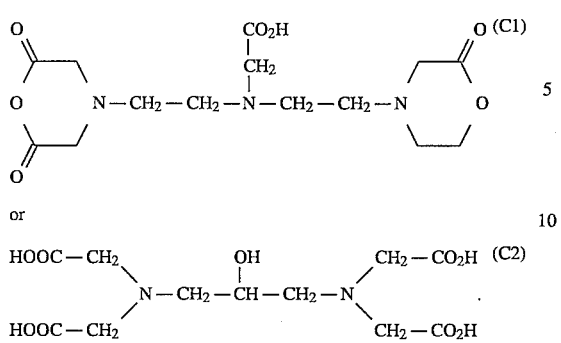

or

8. A biologically active polymer as claimed in claim 5, wherein at least one of the monomer units derived from the formula (II) and/or the formula (III) contains carboxylic acid or sulfonic acid groups and their conjugated bases as water-solubilizing groups.

9. A biologically active polymer as claimed in claim 5, wherein the polymer further comprises a coumarin-containing monomer of the formula (C3) or (C4):

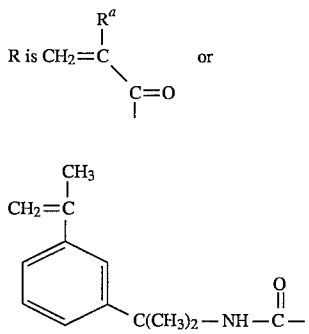

in which

R is 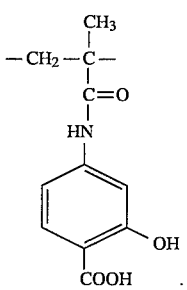 or

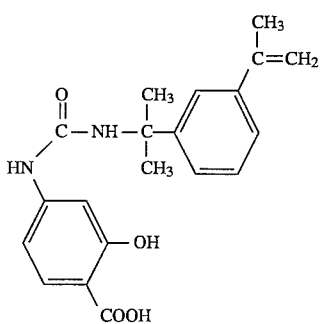

where $R^a$ = H, $CH_3$ where R = H, $CH_3$

10. A biologically active polymer as claimed in claim 5, wherein the polymer comprises the following monomer unit:

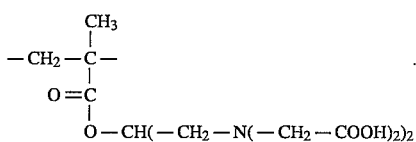

11. A biologically active polymer as claimed in claim 5, wherein the polymer comprises the following monomer unit:

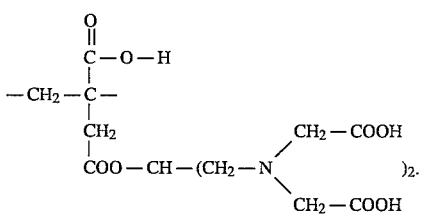

12. A biologically active polymer as claimed in claim 5, wherein the polymer comprises the following monomer unit:

13. A biologically active polymer as claimed in claim 5, wherein the polymer comprises the following monomer unit:

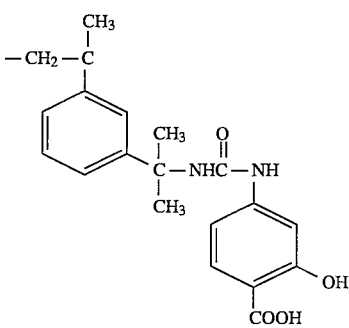

* * * * *